US010751080B2

(12) United States Patent
Kuribara et al.

(10) Patent No.: US 10,751,080 B2
(45) Date of Patent: Aug. 25, 2020

(54) SURGICAL INSTRUMENT AND SURGICAL INSTRUMENT UNIT (71) Applicant: OLYMPUS CORPORATION, Hachioji-shi, Tokyo (JP)

(72) Inventors: Shunsuke Kuribara, Hachioji (JP); Kazuhiro Morisaki, Yokohama (JP)

(73) Assignee: OLYMPUS CORPORATION, Tokyo (JP)

(*) Notice: Subject to any disclaimer, the term of this patent is extended or adjusted under 35 U.S.C. 154(b) by 392 days.

(21) Appl. No.: 15/704,793

(22) Filed: Sep. 14, 2017

(65) Prior Publication Data

US 2018/0000507 A1 Jan. 4, 2018

Related U.S. Application Data

(63) Continuation of application No. PCT/JP2016/067098, filed on Jun. 8, 2016.

(30) Foreign Application Priority Data

Jun. 17, 2015 (JP) ................. 2015-122224

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1442* (2013.01); *A61B 18/1445* (2013.01);
(Continued)

(58) Field of Classification Search
CPC ........ A61B 17/320092; A61B 18/1442; A61B 18/1445; A61B 2017/2825;
(Continued)

(56) References Cited

U.S. PATENT DOCUMENTS 5,954,746 A * 9/1999 Holthaus ........ A61B 17/320092
606/205
6,129,735 A * 10/2000 Okada ............ A61B 17/320068
606/169
(Continued)

FOREIGN PATENT DOCUMENTS

JP 2000-254135 A 9/2000
JP 3791875 B2 6/2006
(Continued)

OTHER PUBLICATIONS

Sep. 13, 2016 International Search Report issued in International Patent Application No. PCT/JP2016/067098.

*Primary Examiner* — Michael F Peffley
(74) *Attorney, Agent, or Firm* — Oliff PLC (57) ABSTRACT

A surgical instrument includes: a clamp section main body which is movable between a close position that is close to a vibration transmission member and an away position that is away from the vibration transmission member; a pressure pad provided on the clamp section main body and provided on a position that is close to the vibration transmission member, the pressure pad being brought into contact with the vibration transmission member when the clamp section main body is in the close position; and a pressing member which is configured to press the vibration transmission member in association with the clamp section main body coming close to the close position, and is configured to decrease pressure of contact between the pressure pad and the vibration transmission member.

11 Claims, 9 Drawing Sheets

(51) Int. Cl.
*A61B 17/28* (2006.01)
*A61B 90/00* (2016.01)
*A61B 17/29* (2006.01)
*A61B 18/00* (2006.01)

(52) U.S. Cl.
CPC ............... *A61B 2017/2825* (2013.01); *A61B 2017/2933* (2013.01); *A61B 2017/2936* (2013.01); *A61B 2017/320093* (2017.08); *A61B 2017/320094* (2017.08); *A61B 2017/320095* (2017.08); *A61B 2018/00994* (2013.01); *A61B 2090/034* (2016.02); *A61B 2090/035* (2016.02)

(58) Field of Classification Search
CPC .... A61B 2017/2933; A61B 2017/2946; A61B 2017/320093; A61B 2017/320094; A61B 2017/320095; A61B 2018/00994; A61B 2090/034; A61B 2090/035
See application file for complete search history.

(56) References Cited

U.S. PATENT DOCUMENTS

| | | | | |
|---|---|---|---|---|
| 6,165,191 | A | * | 12/2000 | Shibata .......... A61B 17/320092 606/169 |
| 6,193,709 | B1 | * | 2/2001 | Miyawaki ...... A61B 17/320092 606/1 |
| 6,454,781 | B1 | * | 9/2002 | Witt ............... A61B 17/320092 606/169 |
| 6,558,376 | B2 | * | 5/2003 | Bishop .......... A61B 17/320092 606/27 |
| 6,569,178 | B1 | | 5/2003 | Miyawaki et al. |
| 2006/0079878 | A1 | | 4/2006 | Houser |
| 2010/0042142 | A1 | | 2/2010 | Cunningham |

FOREIGN PATENT DOCUMENTS

| | | |
|---|---|---|
| JP | 2010-42262 A | 2/2010 |
| JP | 5498624 B2 | 5/2014 |

* cited by examiner

SURGICAL INSTRUMENT AND SURGICAL INSTRUMENT UNIT

CROSS-REFERENCE TO RELATED APPLICATIONS

This application is a Continuation application of PCT Application No. PCT/JP2016/067098, filed Jun. 8, 2016 and based upon and claiming the benefit of priority from prior Japanese Patent Application No. 2015-122224, filed Jun. 17, 2015, the entire contents of all of which are incorporated herein by reference.

BACKGROUND OF THE INVENTION

1. Field of the Invention

The present invention relates to a surgical instrument to grasp a living tissue and to treat the living tissue and a surgical instrument unit to do the same.

2. Description of the Related Art

For example, US2006/0079878A1 discloses a surgical instrument. In this surgical instrument, a clamp section is opened and closed to the distal portion of a vibration transmission member (active blade), and an ultrasonic vibration is transmitted to the vibration transmission member with a living tissue grasped, thereby cutting the grasped living tissue. A pressure pad made of a resin material, which presses the living tissue on the outer surface of the vibration transmission member, is disposed on the clamp portion of the surgical instrument. At the same time when the living tissue is completely cut, the vibration transmission member is brought into contact with the pressure pad with the vibration transmitted to the vibration transmission member.

BRIEF SUMMARY OF THE INVENTION

According to one aspect of the present invention, a surgical instrument includes: a clamp section main body which is movable between a close position that is close to a vibration transmission member and an away position that is away from the vibration transmission member; a pressure pad provided on the clamp section main body and provided on a position that is close to the vibration transmission member, the pressure pad being brought into contact with the vibration transmission member when the clamp section main body is in the close position; and a pressing member which is configured to press the vibration transmission member in association with the clamp section main body coming close to the close position, and is configured to decrease pressure of contact between the pressure pad and the vibration transmission member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of this invention will be described with reference to the drawings.

A first embodiment will be described below with reference to FIG. 1 to FIG. 3.

Figure 1:
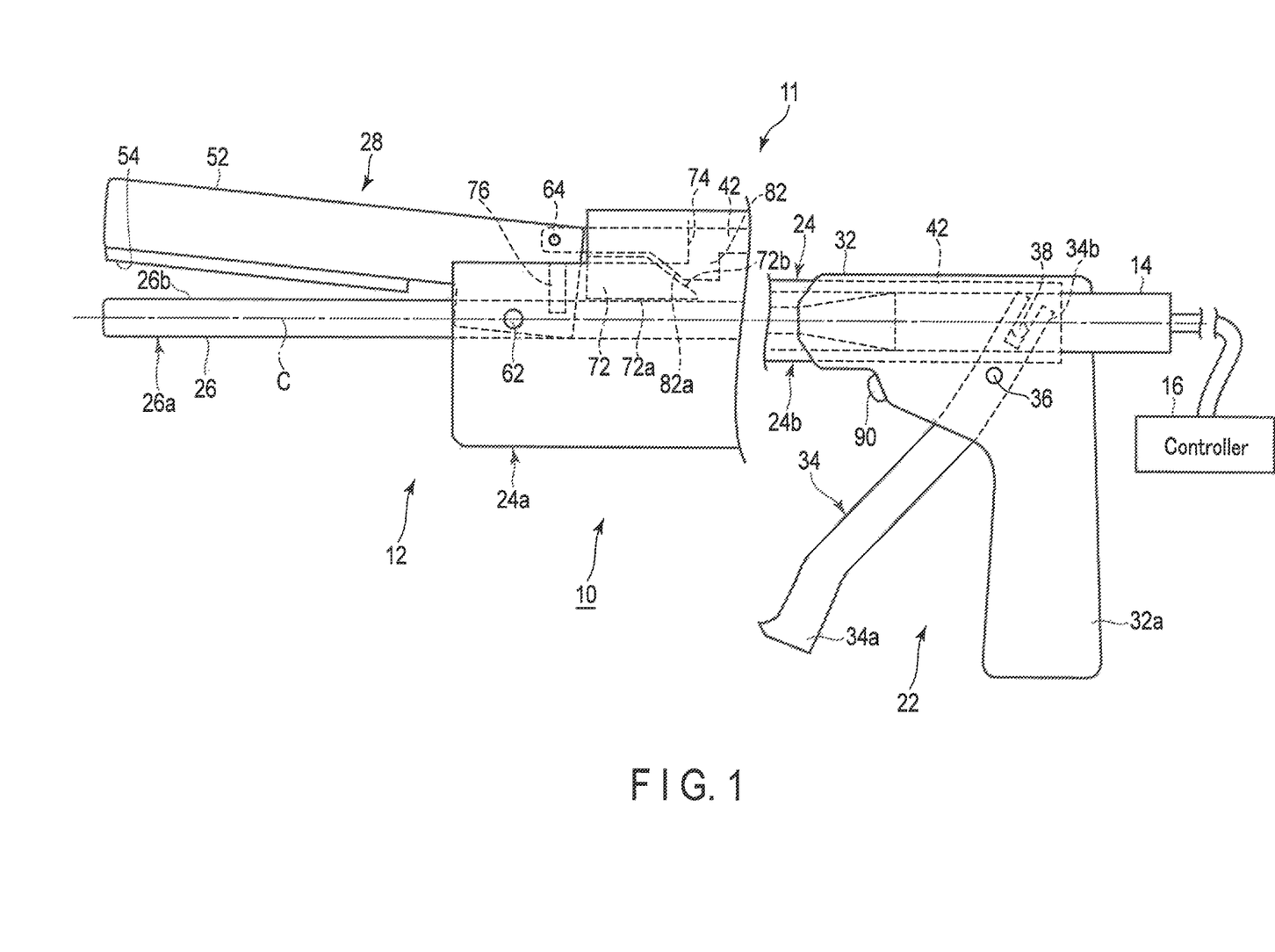
FIG. 1 is a schematic view showing a surgical system according to a first embodiment, in which a clamp section of a surgical instrument is opened to the distal portion of a vibration transmission member.

As shown in FIG. 1, a surgical system 10 according to this embodiment includes a surgical instrument unit 11 and a controller 16. The surgical instrument unit 11 includes a surgical instrument 12 and an ultrasonic transducer 14. The controller 16 includes an energy source (not shown) to supply energy to the ultrasonic transducer 14 to generate an appropriate ultrasonic vibration. The ultrasonic transducer 14 is provided at the distal end of a vibration transmission member 26 (described later), and generates an ultrasonic vibration. Thus, the ultrasonic vibration (longitudinal vibration) can be transmitted to the vibration transmission member 26. Preferably, the energy source of the controller 16 causes the transducer 14 to generate an ultrasonic vibration and allows a high-frequency current to be applied to a living tissue L (see FIG. 6A) which is grasped between the vibration transmission member 26 (described later) serving as a first electrode of the surgical instrument 12 and electrodes 56a and 56b of a clamp section 28 (described later) serving as a second electrode. The controller 16 includes a processor including a CPU, an ASIC or the like.

Figure 2A:
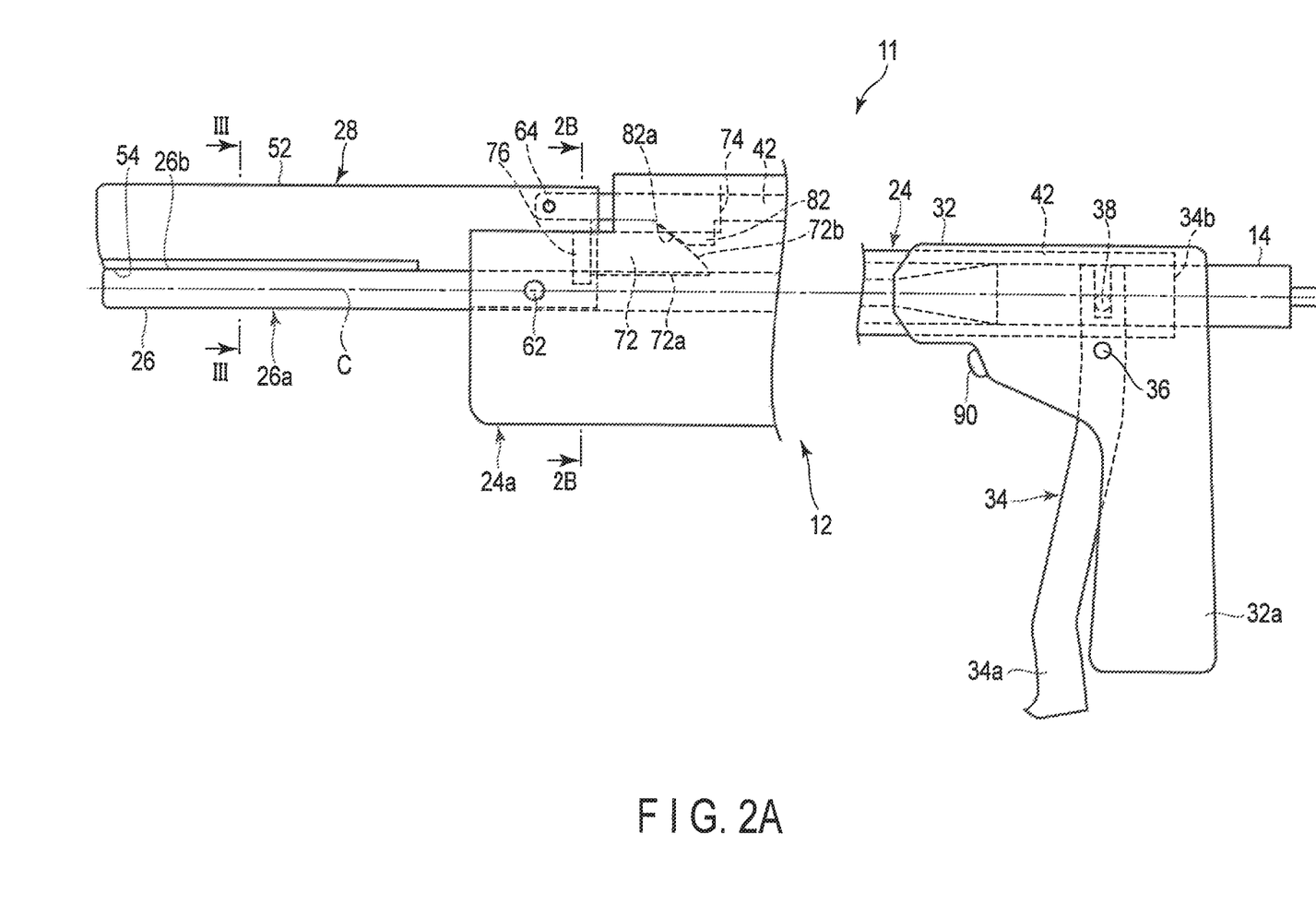
FIG. 2A is a schematic view of the surgical instrument according to the first embodiment, in which the clamp section is closed to the distal portion of the vibration transmission member.
Figure 2B:
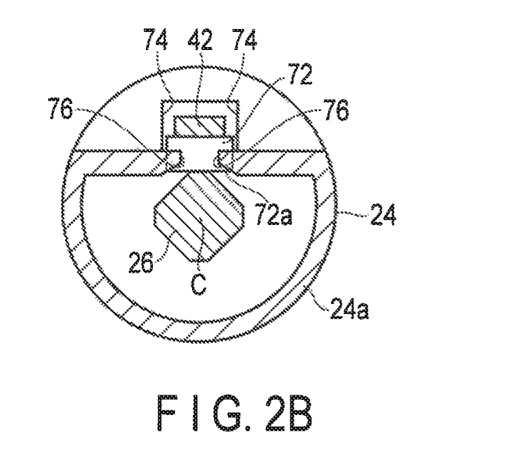
FIG. 2B is a schematic cross-sectional view taken along line 2B-2B of FIG. 2A.
Figure 3:
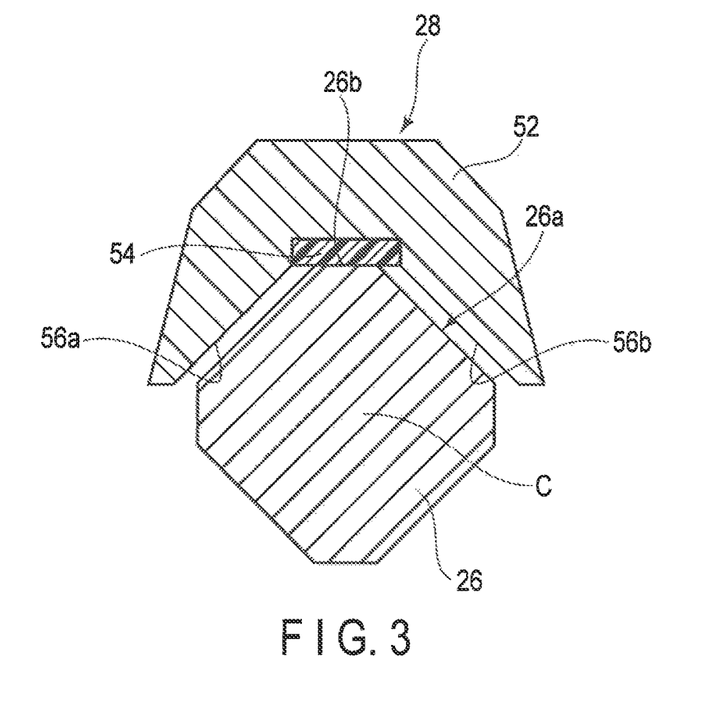
FIG. 3 is a schematic cross-sectional view taken along line III-III of FIG. 2A and showing the clamp section of the surgical instrument according to the first embodiment, which is closed to the distal portion of the vibration transmission member.

As shown in FIG. 1 to FIG. 3, the surgical instrument 12 includes a handle unit 22, a cylindrical sheath 24, the vibration transmission member 26 and the clamp section 28. The sheath 24 has a distal portion 24a and a proximal portion 24b.

As shown in FIG. 1 and FIG. 2A, the handle unit 22 includes a movable handle 34 and a housing 32 with a stationary handle 32a. A driving member 42 is provided in the sheath 24 to operate in association with the manipulation of the movable handle 34. It is preferable that the driving member 42 be formed cylindrically and concentrically with the sheath 24. The movable handle 34 can be pivoted on a pivot 36 with respect to the housing 32 if an operation section 34a is operated. The movable handle 34 can be moved between an away position (open position) which is away from the stationary handle 32a of the housing 32 as shown in FIG. 1 and a close position (closed position) which is close to the stationary handle 32a of the housing 32 as shown in FIG. 2A. In this embodiment, an example is given in which the clamp section 28 is in a position that is away from the distal portion (treatment portion) 26a of the vibration transmission member 26 when the movable handle 34 is in the away position (separate position), and the clamp section 28 is in a position close to the distal portion 26a of the vibration transmission member 26 when the movable handle 34 is in the close position (adjacent position), which will be described later. The surgical instrument 12 may have a structure in which the clamp section 28 is in a position that is close to the distal portion (treatment portion) 26a of the vibration transmission member 26 when the movable handle 34 is in the away position, and the clamp section 28 is in a position that is away from the distal portion 26a of the vibration transmission member 26 when the movable handle 34 is in the close position.

An end portion 34b of the movable handle 34, which is inside the housing 32, can be moved between the position shown in FIG. 1 and the position shown in FIG. 2A if the movable handle 34 is pivoted on the pivot 36. The end portion 34b is connected to the driving member 42 through, e.g. a driving pin 38.

When the operation section 34a of the movable handle 34 is made close to the stationary handle 32a of the housing 32, the movable handle 34 pivots on the pivot 36 and accordingly the driving pin 38 advances to the distal side of the sheath 24. When the movable handle 34 is separated from the stationary handle 32a of the housing 32, the movable handle 34 turns on the pivot 36 and accordingly the driving pin 38 retreats to the proximal side of the sheath 24.

The clamp section 28 is pivotably supported by the distal portion 24a of the sheath 24. As shown in FIG. 2A and FIG. 3, the clamp section 28 includes a clamp section main body (pivoting body) 52, a pressure pad 54 provided on the main body 52, and a pair of electrodes 56a and 56b provided on the main body 52.

The main body 52 of the clamp section 28 is pivotably supported by a main rotation shaft 62 with respect to the distal portion 24a of the sheath 24. The main body 52 is pivotably supported by a movable rotation shaft (distal-side rotation shaft) 64 with respect to the distal portion 24a of the driving member 42. When the driving member 42 advances with respect to the sheath 24 by manipulating the movable handle 34 toward the housing 32, the driving member 42 pushes the main body 52 toward the front of the sheath 24 substantially in parallel to a central axis C by the movable rotation shaft 64. The relationship in position between the main rotation shaft 62 and the main body 52 does not vary and thus the main body 52 is closed toward the distal portion 26a of the vibration transmission member 26. On the other hand, when the driving member 42 retreats with respect to the sheath 24 by manipulating the movable handle 34, the driving member 42 pulls the main body 52 toward the rear of the sheath 24 in parallel to the central axis C by the movable rotation shaft 64. Thus, the main body 52 is opened toward the distal portion 26a of the vibration transmission member 26. In other words, the main body 52 can be moved between a close position (closed position) which is close to the vibration transmission member 26 and an away position (open position) which is away from the distal the vibration transmission member 26.

As the main body 52 of the clamp section 28, for example, at least two bodies such as publicly-known seesaw jaws and wiper jaws, can be used.

The pressure pad 54 of the main body 52 is provided close to and opposite to the treatment surface 26b of the distal portion 26a of the vibration transmission member 26. The pressure pad 54 is provided between the electrodes 56a and 56b. The pressure pad 54 is brought into contact with the treatment surface 26b of the distal portion 26a of the vibration transmission member 26 when the main body 52 is in the close position, and the pressure pad 54 is separated from the treatment surface 26b of the distal portion 26a of the vibration transmission member 26 as the main body 52 moves from the away position. The pressure pad 54 is made of a material having electrical insulation properties, heat resistance properties and wear resistance properties. As the pressure pad 54, for example, PTFE can be used.

In this embodiment, when the clamp section 28 is in the close position, the treatment surface 26b of the distal portion 26a of the vibration transmission member 26 can be brought into contact with the pressure pad 54, cannot be brought into contact with the electrodes 56a and 56b. If, therefore, the living tissue L is grasped between the treatment surface 26b of the distal portion 26a of the vibration transmission member 26, which serves as one electrode, and the electrodes 56a and 56b of the clamp section 28 which serve as the other electrode, bipolar treatment can be performed for the living tissue L.

Instead of the electrodes 56a and 56b, a heater can be used; alternatively, the same material as that of the pressure pad 54 can be provided on the surface.

The vibration transmission member 26 is inserted through the sheath 24. The vibration transmission member 26 is formed substantially like a rod by a material having a good vibration transmittance performance, such as a titanium alloy material and an aluminum alloy material. The vibration transmission member 26 has conductivity when the vibration transmission member 26 is used as a high-frequency electrode, as described in this embodiment. It is favorable that the vibration transmission member 26 be provided on the central axis C of the sheath 24. The ultrasonic transducer 14 attached to the proximal end of the vibration transmission member 26 transmits a vibration with an appropriate frequency from the proximal end of the vibration transmission member 26 toward the distal end of the vibration transmission member 26. The length of the vibration transmission member 26 is thus set by the frequency of the vibration output from the ultrasonic transducer 14. The distal end of the vibration transmission member 26 is particularly set to the antinode position of the vibration for appropriate treatment for the living tissue L. In other words, the vibration transmission member 26 is so formed that the distal end of the vibration transmission member 26 is in the antinode position of the vibration when the ultrasonic transducer 14 provided at the proximal end of the vibration transmission member 26 generates an ultrasonic vibration and transmits the ultrasonic vibration to the vibration transmission member 26. It is favorable that a ring-shaped member having electrical insulation properties and heat resistance properties be provided between the vibration transmission member 26 and the inner surface of the sheath 24 in a node position.

As shown in FIG. 1 to FIG. 2B, a pressing member 72 is provided between a portion close to the distal portion of the driving member 42 and the vibration transmission member 26. The pressing member 72 is formed of, e.g. a resin material as a material having electrical insulation properties. It is favorable that the pressing member 72 be formed of a material having heat resistance properties and wear resistance properties. The pressing member 72 employs a material having good electrical insulation properties, heat resistance properties and wear resistance properties, such as PTFE. It is favorable that the pressing member 72 employ a material from which friction is harder to generate than the pressure pad 54. It is thus favorable that the pressing member 72 employ, e.g. a material which is harder than the pressure pad 54.

As shown in FIG. 1 and FIG. 2A, in this embodiment, the pressing member 72 is formed such that a longitudinal section of the pressing member 72 is shaped substantially like a trapezoid. The pressing member 72 has a contact surface 72a that contacts the vibration transmission member 26 and an inclined surface (pressing surface) 72b opposed to the contact surface 72a. In this embodiment, the normal to the inclined surface 72b is directed outward in a radial direction with respect to the central axis C and directed to the rear of the sheath 24. The inclined surface 72b may be a flat surface or a curved surface. It is preferable to form the inclined surface 72b not concavely but convexly particularly when the inclined surface 72b is a curved surface.

As shown in FIG. 1 to FIG. 2B, the sheath 24 covers the outer periphery of the driving member 42, and the pressing member 72 is provided at the proximal side of the sheath 24 rather than the distal end of the sheath 24. A pair of walls 74 is formed in the sheath 24 to inhibit the pressing member 72 from moving in a circumferential direction with respect to the sheath 24 and the vibration transmission member 26. A stopper 76 is formed at the distal end of the sheath 24 to inhibit the pressing member 72 from dropping from the distal end of the sheath 24. The pair of walls 74 and stopper 76 and a convex portion 82 (described later) of the driving member 42 are each used as a guide that is able to move the pressing member 72 with respect to the vibration transmission member 26 within a predetermined range.

In a position of the driving member 42 which is adjacent to the inclined surface 72b of the pressing member 72, a convex portion (pressing portion) 82 having an inclined surface 82a that can press the inclined surface 72b of the pressing member 72 is formed. The inclined surface 82a of the convex portion 82 presses the inclined surface 72b of the pressing member 72 as the driving member 42 advances and the clamp section 28 comes close to the close position. Accordingly, the contact surface 72a of the pressing member 72 presses the vibration transmission member 26. On the other hand, the inclined surface 82a of the convex portion 82 releases a pressing of the inclined surface 82a on the inclined surface 72b as the clamp section 28 comes close to the away position and thus the contact surface 72a of the pressing member 72 releases a pressing of the contact surface 72a on the vibration transmission member 26. In this case, the pressing member 72 is placed on the vibration transmission member 26. In other words, the pressing member 72 is movable between a pressing position in which the vibration transmission member 26 is pressed and a pressing release position in which the pressing on the vibration transmission member 26 is released, in association with the movement of the main body 52. Then, the pressing member 72 is movable to the pressing release position from the pressing position, in association with the movement of the main body 52 from the close position to the away position.

It is favorable that when a vibration is generated in the ultrasonic transducer 14, and is transmitted to the vibration transmission member 26, the pressing member 72 should be placed in a vibration node position of the vibration transmission member 26, especially in a first-vibration node position from the distal end of the vibration transmission member 26. This position is maintained by, e.g. the walls 74, stopper 76 and convex portion 82.

As shown in FIG. 1 and FIG. 2A, the housing 32 is provided with a switch 90. When the switch 90 is depressed, the ultrasonic transducer 14 generates an ultrasonic vibration, and a bipolar-type high-frequency is output between the vibration transmission member 26 as the first electrode and the electrodes 56a and 56b as the second electrode. Thus, as in the publicly-known art, the living tissue L grasped between the vibration transmission member 26 and the electrodes 56a and 56b is cut chiefly by transmitting the ultrasonic vibration to the living tissue L while coagulating the living tissue L chiefly by outputting the high frequency. In particular, if the living tissue L is a blood vessel, the surgical instrument 12 is cut while being sealed.

An operation of the surgical system 10 according to this embodiment will be described below.

An operator brings the movable handle 34 close to the stationary handle 32a of the housing 32 and closes it. The driving member 42 is advanced to the sheath 24 and the proximal end of the clamp section 28 is advanced by the driving member 42. Accordingly, the clamp section 28 pivots on the main rotation shaft 62 and the movable rotation shaft 64, and comes close to the vibration transmission member 26 and closes, thereby catching the living tissue L between the pressure pad 54 and the vibration transmission member 26. At this time, the contact surface 72a of the pressing member 72 can be brought into contact with the outer periphery of the vibration transmission member 26 (especially a position set to correspond to the first-vibration node position from the distal end of the vibration transmission member 26) and the foregoing ring-shaped member.

Depending on the thickness of the living tissue L, the presence of the living tissue L inhibits the inclined surface 72b of the pressing member 72 from being pressed by the inclined surface 82a of the convex portion 82 of the driving member 42. Thus, when the living tissue L is present between the pressure pad 54 of the clamp section 28 and the vibration transmission member 26, the vibration transmission member 26 is not pressed by the contact surface 72a of the pressing member 72, depending on the thickness of the living tissue L. When the contact surface 72a of the pressing member 72 is simply in contact with the outer surface of the vibration transmission member 26, the vibration transmission member 26 is hardly bent by the pressing member 72 because the weight of the pressing member 72 is small.

When the operator depresses the switch 90, the ultrasonic transducer 14 generates an ultrasonic vibration, and a bipolar-type high-frequency is output between the vibration transmission member 26 as the first electrode and the electrodes 56a and 56b as the second electrode, which are separated from the vibration transmission member 26. Thus, the living tissue L grasped between the vibration transmission member 26 and the electrodes 56a and 56b is cut mainly by the operation of transmitting the ultrasonic vibration to the living tissue L while coagulating the living tissue L mainly by the operation of outputting the high frequency. In particular, if the living tissue L is a blood vessel, the surgical instrument 12 is cut while being sealed.

Even though the contact surface 72a of the pressing member 72 is placed on the outer peripheral surface of the vibration transmission member 26 or in contact with the outer surface of the vibration transmission member 26, a contact place of the contact surface 72a of the pressing member 72 is in the node position of the vibration transmission member 26. Therefore, even though a vibration is transmitted to the vibration transmission member 26, the contact surface 72a of the pressing member 72 is prevented from being worn.

Since the operator brings the movable handle 34 close to the stationary handle 32a of the housing 32, the driving member 42 advances to the sheath 24 as the living tissue L is cut while being coagulated. Then, the pressure pad 54 gradually comes closer to the treatment surface 26b of the distal portion 26a of the vibration transmission member 26.

To bring the treatment surface 26b of the distal portion 26a of the vibration transmission member 26 into contact with the pressure pad 54 while a vibration is transmitting to the vibration transmission member 26, is a guide for completing cutting the living tissue L while being coagulated. It is thus designed that after the treatment surface 26b of the distal portion 26a of the vibration transmission member 26 is brought into contact with the pressure pad 54, the periphery of the vibration transmission member 26 is pressed by the contact surface 72a of the pressing member 72. In other words, when the main body 52 of the clamp section 28 is in the close position, the pressure pad 54 can be brought into contact with the distal portion 26a of the vibration transmission member 26.

Since the stopper 76 inhibits the pressing member 72 from advancing to the sheath 24, the convex portion 82 of the driving member 42 presses the pressing member 72 on the vibration transmission member 26 in accordance with the advance of the driving member 42. Then, when the treatment surface 26b of the distal portion 26a of the vibration transmission member 26 is brought into contact with the pressure pad 54, the periphery of the vibration transmission member 26 is pressed by the contact surface 72a of the pressing member 72.

The timing with which the distal portion 26a of the vibration transmission member 26 is brought into contact with the pressing pad 54 and the timing with which the periphery of the vibration transmission member 26 is pressed by the contact surface 72a of the pressing member 72 are shifted by appropriately adjusting the position and size of the convex portion 82 of the driving member 42, the size and shape of, e.g. the pressing member 72, and the like. It is particularly favorable that for example, the driving member 42 and the pressing member 72 be set such that the periphery of the vibration transmission member 26 is pressed by the contact surface 72a of the pressing member 72 immediately after the distal portion 26a of the vibration transmission member 26 is brought into contact with the pressing pad 54.

After the distal portion 26a of the vibration transmission member 26 is brought into contact with the pressing pad 54 as described above, the contact surface 72a of the pressing member 72 loads pressing force on the outside of the vibration transmission member 26. Then, the distal portion 26a of the vibration transmission member 26, more specifically, a portion (the open end of the vibration transmission member 26) of the distal side than the portion (the first-vibration node position from the distal end of the vibration transmission member 26) pressed by the contact surface 72a of the pressing member 72 is bent in a direction away from the pressure pad 54 of the clamp section 28. Since the vibration transmission member 26 is bent in a direction away from the pressure pad 54 of the clamp section 28 as described above, the pressure of contact between the pressure pad 54 and the vibration transmission member 26 is decreased with a vibration transmitted to the vibration transmission member 26. The pressure pad 54 and the vibration transmission member 26 may contact each other or the contact can be released. Therefore, while a vibration is continuously transmitted to the vibration transmission member 26, the living tissue L can be completely cut while being coagulated, and the pressure pad 54 can be prevented from being worn due to the vibration of the vibration transmission member 26.

If the contact surface 72a of the pressing member 72 is in contact with the vibration transmission member 26 in the vibration node position of the vibration transmission member 26 when a vibration is transmitted to the vibration transmission member 26, the vibration is not transmitted to the contact surface 72a of the pressing member 72. Thus, the pressure pad 54 is inhibited from being worn, as is the pressing member 72.

After the depression of the switch 90 is released to stop the transmission of vibration to the vibration transmission member 26 and stop the high-frequency output, the movable handle 34 is separated from and opened to the stationary handle 32a of the housing 32. The driving member 42 is retreated with respect to the sheath 24 and the proximal end of the clamp section 28 is retreated by the driving member 42. Accordingly, the clamp section 28 is opened to the vibration transmission member 26. Since the convex portion 82 of the driving member 42 is retreated to the sheath 24, the pressing of the outer surface of the vibration transmission member 26 by the contact surface 72a of the pressing member 72 is also released.

The following can be said from the surgical instrument 12 according to this embodiment described above.

When the clamp section 28 is disposed in a close position to the vibration transmission member 26, the distal portion 26a of the vibration transmission member 26 can be first brought into contact with the pressure pad 54 and then the outer surface (e.g. the vibration node position) of the vibration transmission member 26 can be pressed by the contact surface 72a of the pressing member 72. Since the distal portion (open end) 26a of the vibration transmission member 26 is bent by elastic deformation and moved in a direction away from the pressure pad 54 of the clamp section 28, the pressure between the distal portion 26a of the vibration transmission member 26 and the pressure pad 54 can be inhibited from increasing. In other words, the pressing member 72 can press the vibration transmission member 26 in association with the main body 52 coming close to the close position to decrease the pressure of contact between the pressure pad 54 and the vibration transmission member 26. Therefore, even though the distal portion 26a of the vibration transmission member 26 and the pressure pad 54 continues to contact each other, when a vibration is continuously transmitted to the vibration transmission member 26, the pressure pad 54 can be inhibited from being worn by the vibration of the vibration transmission member 26. Then, the pressing member 72 can release the pressing on the vibration transmission member 26 in association with the main body 52 coming close to the distal position.

Figure 4:
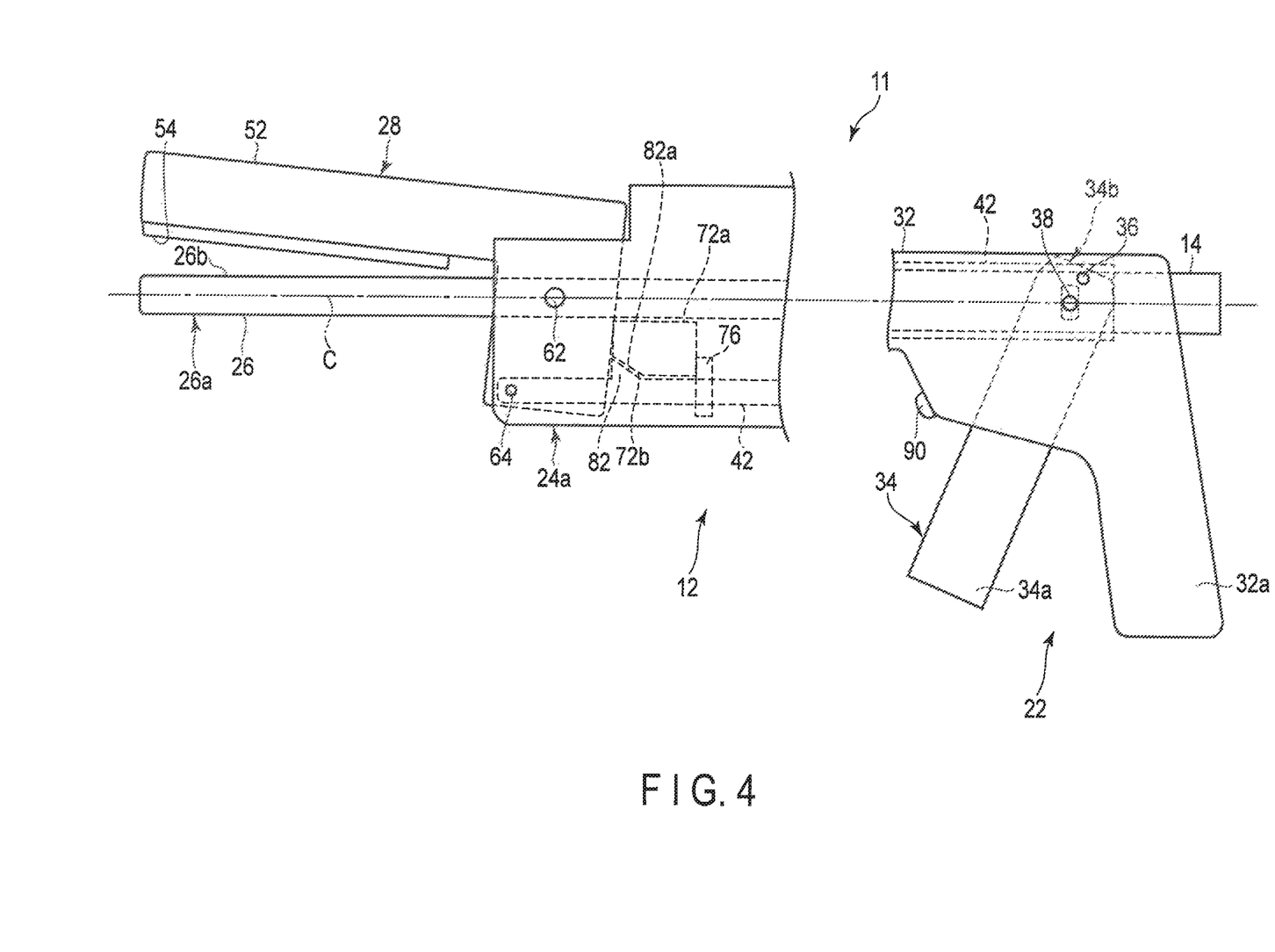
FIG. 4 is a schematic view showing a surgical instrument according to a modification to the first embodiment, in which a clamp section is opened to the distal portion of a vibration transmission member.
Figure 5:
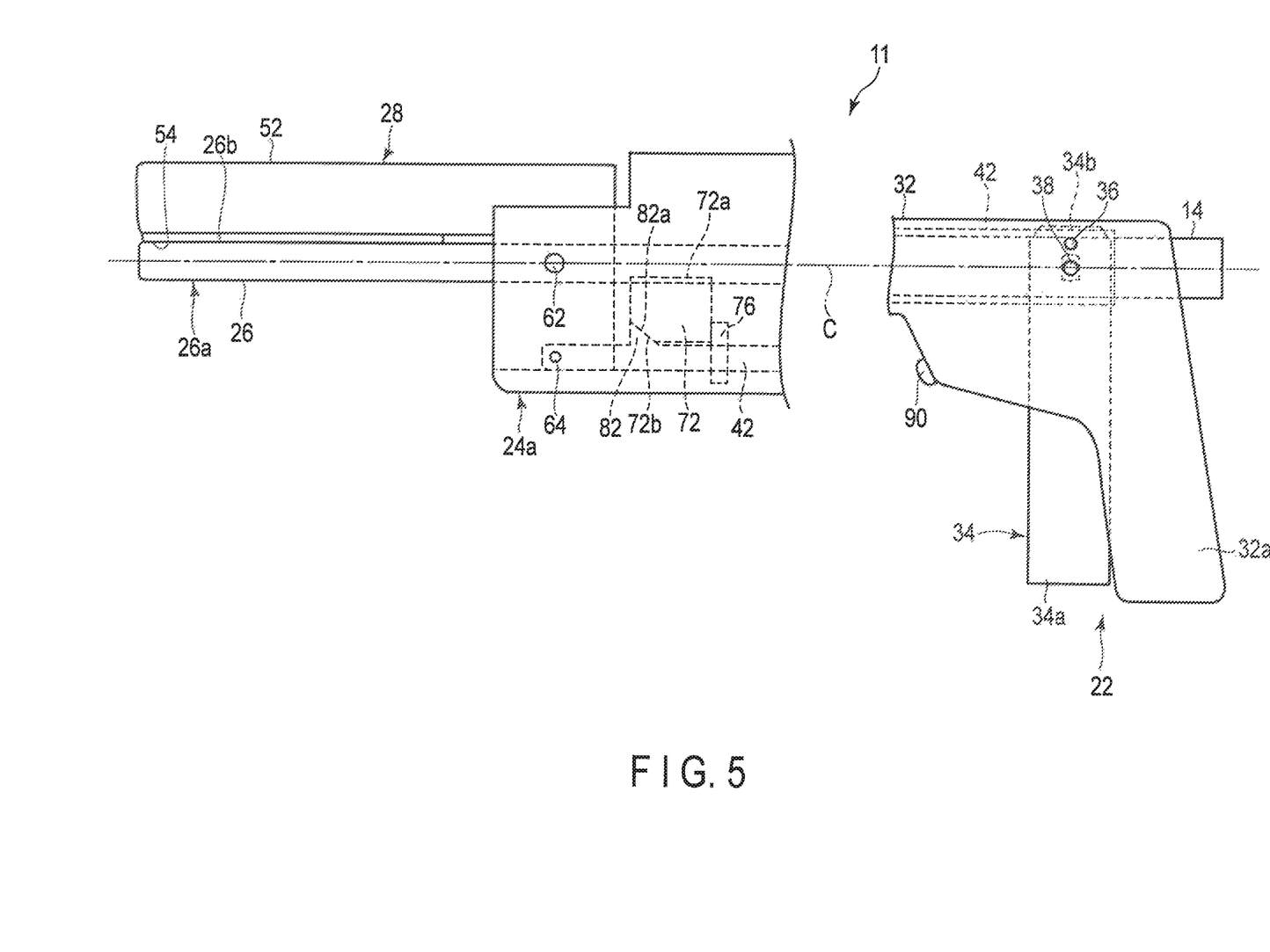
FIG. 5 is a schematic view of the surgical instrument according to the modification to the first embodiment, in which the clamp section is closed to the distal portion of the vibration transmission member.

A modification to the first embodiment will be described below with reference to FIG. 4 and FIG. 5.

In the first embodiment, it is described that the clamp section 28 is disposed in the closed position when the driving member 42 is advanced and the clamp section 28 is disposed in the open position when the driving member 42 is retreated. In addition, it is favorable that the clamp section 28 be disposed in a position away from and opened to the distal portion 26a of the vibration transmission member 26 when the driving member 42 is advanced, and the clamp section 28 be disposed in a position closed to the distal portion 26a of the vibration transmission member 26 when the driving member 42 is retreated, as shown in FIG. 4 and FIG. 5.

In this case, the direction of the inclined surface 82a at the distal portion of the driving member 42 is opposite to that of the inclined surface 82a shown in FIG. 1 and FIG. 2A. The sheath 24 includes walls 74 (not shown here) to inhibit the pressing member 72 from moving in the circumferential direction and a stopper 76 to inhibit the pressing member 72 from moving to the proximal side.

A second embodiment will be described below with reference to FIG. 6A to FIG. 6C. The second embodiment is a modification to the first embodiment including the foregoing modification, and the same symbols will be used to denote the same members as those of the first embodiment and their detailed descriptions will be omitted.

In the second embodiment, the sheath 24 includes neither the walls 74 nor the stopper 76, and the pressing member 72 can be guided in a direction close to the central axis C and a direction separated from the central axis C.

Figure 6A:
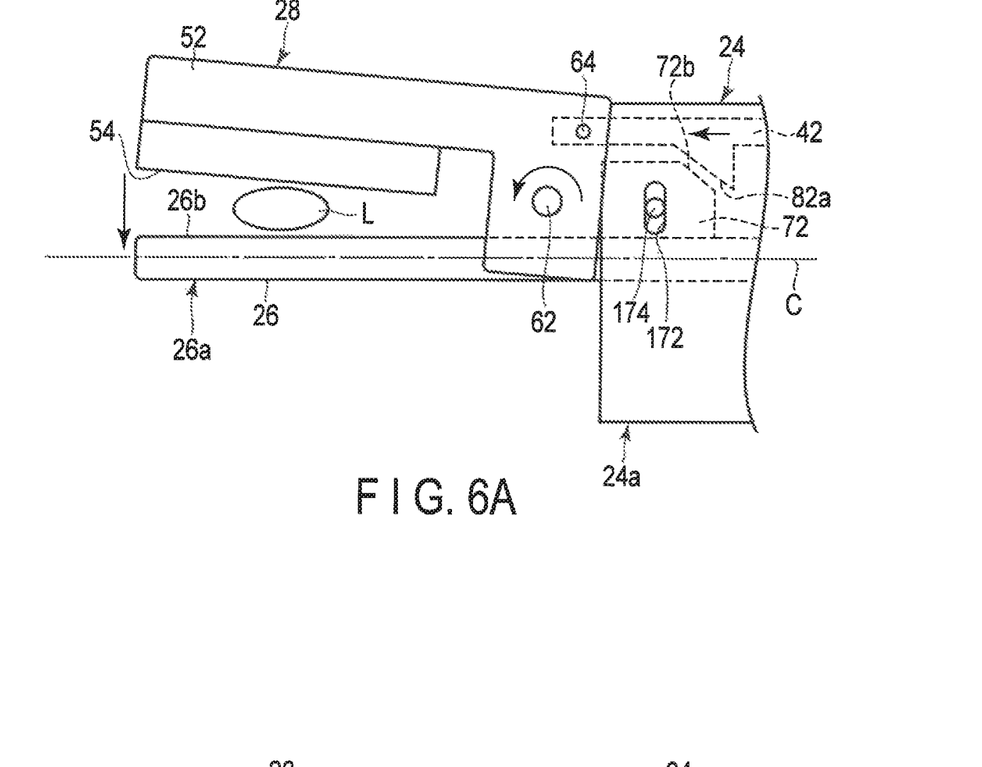
FIG. 6A is a schematic view showing a surgical instrument according to a second embodiment, in which a living tissue is grasped while a clamp section is being closed to the distal portion of a vibration transmission member.
Figure 6B:
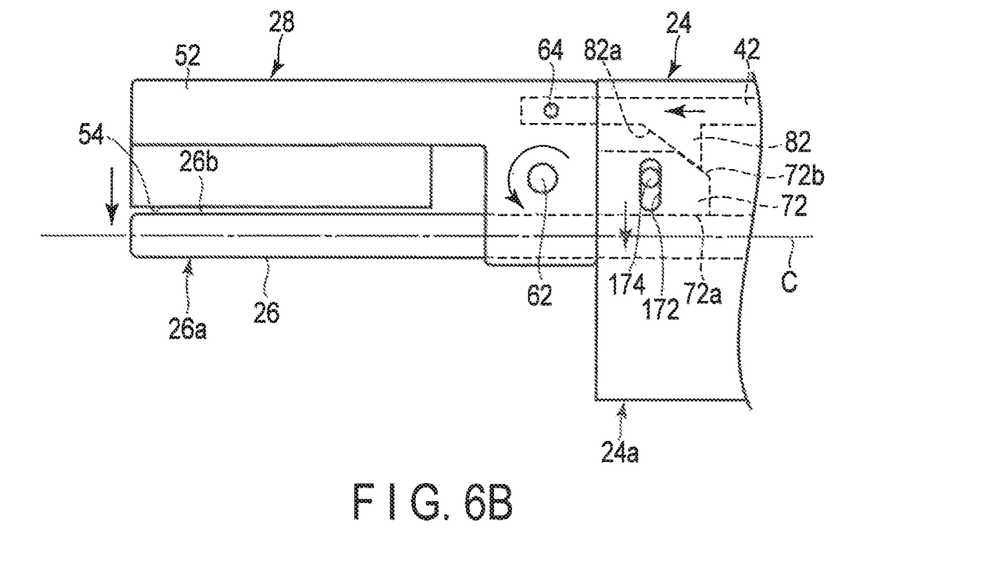
FIG. 6B is a schematic view of the surgical instrument according to the second embodiment, in which the clamp section is closed to the distal portion of the vibration transmission member to complete cutting the living tissue, and the vibration transmission member is pressed by a pressing member to be separated from a pressure pad.
Figure 6C:
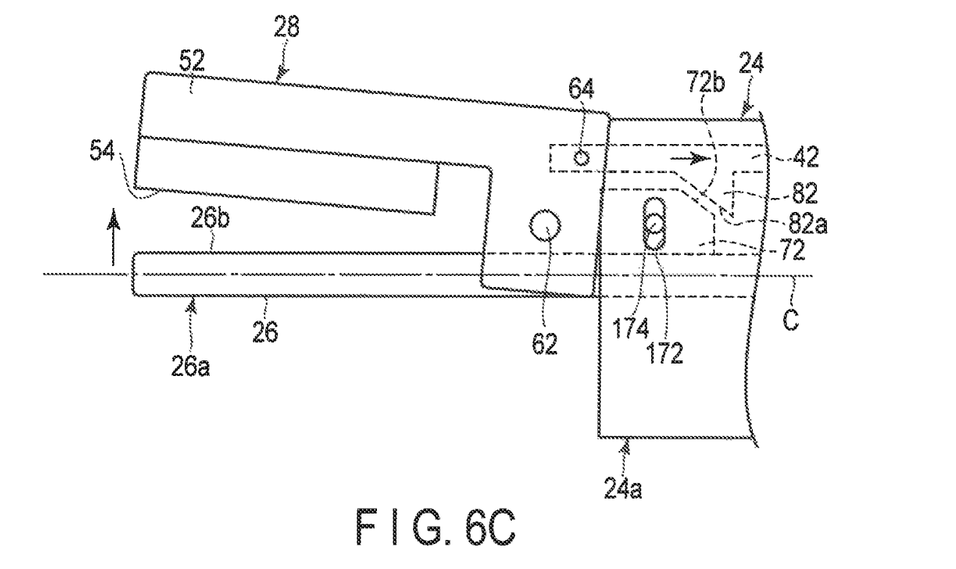
FIG. 6C is a schematic view of the surgical instrument according to the second embodiment, in which the clamp section is opened to the distal portion of the vibration transmission member.

As shown in FIG. 6A to FIG. 6C, a guide (guide hole) 172 is formed in the pressing member 72. It is favorable that the guide 172 penetrates the pressing member 72 in a direction orthogonal or substantially orthogonal to the central axis C. The guide 172 is a long hole that is elongated in a direction orthogonal to the central axis C in FIG. 6A to FIG. 6C, and the guide 172 is satisfactory unless the long hole is elongated in a direction parallel to the central axis C. In other words, the longitudinal direction of the guide 172 can be set as appropriate.

The guide 172 is provided with, for example, a pin 174 protruding from the sheath 24. Since the relationship in position between the sheath 24 and the pin 174 does not vary, the pressing member 72 can be moved in a direction close to the central axis C and a direction separated from the central axis C. Thus, the range of movement of the pressing member 72 to the sheath 24 is determined by the guide 172.

The operation of a surgical system 10 according to the second embodiment will be briefly described below.

As shown in FIG. 6A, the clamp section 28 is closed by operating the movable handle 34 (see FIG. 1 and FIG. 2A) to grasp a living tissue L between the pressure pad 54 of the clamp section 28 and the vibration transmission member 26. The pressing member 72 can be moved along the guide 172. As in the first embodiment, the contact surface 72a of the pressing member 72 may contact the vibration transmission member 26, but the presence of the living tissue L inhibits the pressing member 72 from being pressed by the driving member 42 and inhibits the vibration transmission member 26 from being pressed by the contact surface 72a of the pressing member 72.

When the switch 90 (see FIG. 1 and FIG. 2A) is depressed, the ultrasonic transducer 14 generates an ultrasonic vibration, and the vibration is transmitted to the vibration transmission member 26, and a bipolar-type high-frequency is output between the vibration transmission member 26 as the first electrode and the electrodes 56a and 56b as the second electrode.

Even though the contact surface 72a of the pressing member 72 is in contact with the outer surface of the vibration transmission member 26, the guide 172 inhibits the pressing member 72 from moving, and the contact surface 72a of the pressing member 72 is in the vibration node position of the vibration transmission member 26 that the contact surface 72a of the pressing member 72 is in contact with the outer periphery of the vibration transmission member 26. Therefore, even though a vibration is transmitted to the vibration transmission member 26, the contact surface 72a of the pressing member 72 is prevented from being worn.

As the living tissue L is cut while being coagulated, the driving member 42 advances to the sheath 24 and, as shown in FIG. 6B, the treatment surface 26b of the distal portion 26a of the vibration transmission member 26 is brought into contact with the pressure pad 54. The convex portion 82 of the driving member 42 presses the pressing member 72 onto the vibration transmission member 26 as the driving member 42 advances. After the treatment surface 26b of the distal portion 26a of the vibration transmission member 26 is brought into contact with the pressure pad 54, the periphery of the vibration transmission member 26 is pressed by the contact surface 72a of the pressing member 72.

After the distal portion 26a of the vibration transmission member 26 is brought into contact with the pressure pad 54 as described above, the contact surface 72a of the pressing member 72 loads pressing force on the outside of the vibration transmission member 26. Then, the distal portion 26a of the vibration transmission member 26, more specifically, a portion (the open end of the vibration transmission member 26) of the distal side than the portion pressed by the contact surface 72a of the pressing member 72 is bent in a direction away from the pressure pad 54 of the clamp section 28. Since the vibration transmission member 26 is bent in a direction away from the pressure pad 54 of the clamp section 28 as described above, the pressure of contact between the pressure pad 54 and the vibration transmission member 26 is decreased with a vibration transmitted to the vibration transmission member 26. The pressure pad 54 and the vibration transmission member 26 may contact each other or the contact can be released. Therefore, while a vibration is continuously transmitted to the vibration transmission member 26, the pressure pad 54 can be prevented from being worn due to the vibration of the vibration transmission member 26.

After the depression of the switch 90 is released to stop the transmission of vibration to the vibration transmission member 26 and stop the high-frequency output, the movable handle 34 is separated from and opened to the stationary handle 32a of the housing 32, as shown in FIG. 6C. The driving member 42 is retreated to the sheath 24 and the proximal end of the clamp section 28 is retreated by the driving member 42. Accordingly, the clamp section 28 is opened to the vibration transmission member 26. Since the convex portion 82 of the driving member 42 is retreated to the sheath 24, the pressing of the outer surface of the vibration transmission member 26 by the contact surface 72a of the pressing member 72 is also released. Since the pressing member 72 is in a release state where the pressing member 72 can be moved along the guide 172, the pressure pad 54 is simply in contact with the outer surface of the vibration transmission member 26 or is separated from the outer surface of the vibration transmission member 26.

Even with the use of the structure in which the clamp section 28 is opened to the vibration transmission member 26 when the driving member 42 advances and the clamp section 28 is closed to the vibration transmission member 26 when the driving member 42 is retreated as described in the modification to the first embodiment, the relationship between the pin 174 and the guide 172 can be adopted as well.

A third embodiment will be described below with reference to FIG. 7A and FIG. 7B. The third embodiment is a modification to the first embodiment including the modification and the second embodiment, and the same symbols will be used to denote the same members as those of the first and second embodiments and their detailed descriptions will be omitted.

Unlike in the first and second embodiments, in the third embodiment, the convex portion 82 is eliminated from the driving member 42 and instead a cam groove 282 is formed as a pressing portion in the driving member 42. Furthermore, a cam pin 272 is formed in the pressing member 72.

Figure 7A:
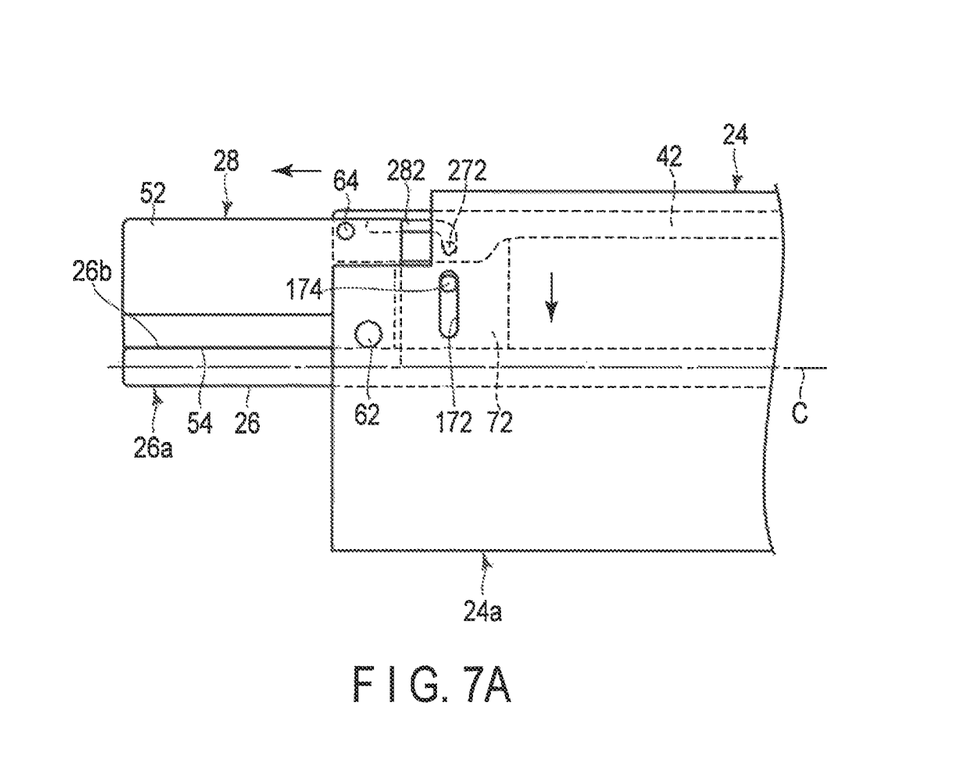
FIG. 7A is a schematic view showing a surgical instrument according to a third embodiment, in which a clamp section is closed to the distal portion of a vibration transmission member to complete cutting a living tissue, and the vibration transmission member is pressed by a pressing member to be separated from a pressure pad.

When the clamp section 28 is disposed in the close position as shown in FIG. 7A, the cam groove 282 presses the cam pin 272 toward the central axis C at the proximal end of the cam groove 282. Accordingly, the contact surface 72a of the pressing member 72 moves toward the central axis C along the pin 174 by the guide 172.

Figure 7B:
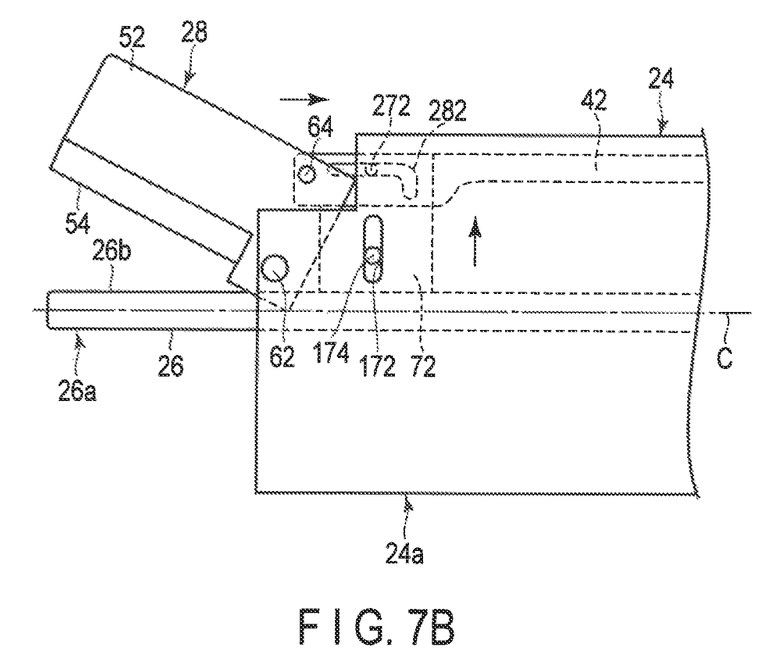
FIG. 7B is a schematic view of the surgical instrument according to the third embodiment, in which the clamp section is opened to the distal portion of the vibration transmission member.

When the clamp section 28 is disposed in the away position as shown in FIG. 7B, the cam groove 282 is formed between the distal end and proximal end of the cam groove 282. In this case, the cam pin 272 is in the upper part of FIG. 7B as compared with the case shown in FIG. 7A. Thus, the pressing member 72 moves in a direction away from the central axis C.

Even with the use of the structure in which the clamp section 28 is opened to the vibration transmission member 26 when the driving member 42 advances and the clamp section 28 is closed to the vibration transmission member 26 when the driving member 42 is retreated as described in the modification to the first embodiment, the relationship between the pin 174 and the guide 172 can be adopted as well, as can be the relationship between the cam pin 272 and the cam groove 282.

A fourth embodiment will be described below with reference to FIG. 8A to FIG. 8C. The fourth embodiment is a modification to the first embodiment including the modification, and the second and third embodiments, and the same symbols will be used to denote the same members as those of the first, second and third embodiments and their detailed descriptions will be omitted.

Unlike in the first and second embodiments, in the fourth embodiment, the pressing member 72 is disposed in the main body 52 of the clamp section 28.

Figure 8A:
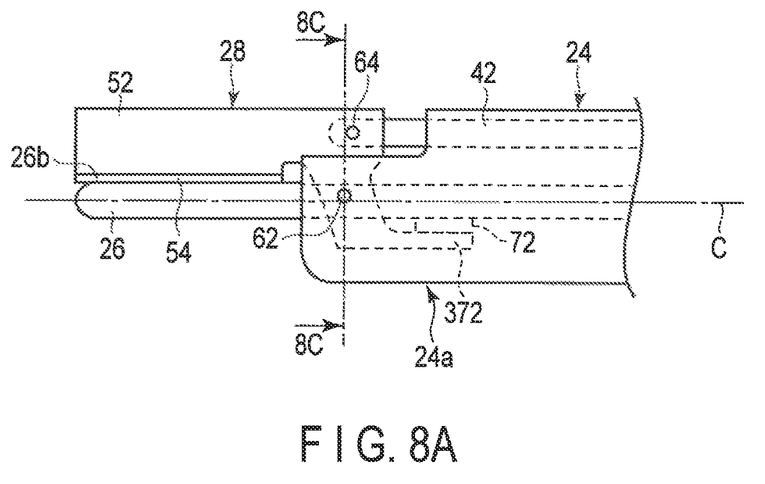
FIG. 8A is a schematic view showing a surgical instrument according to a fourth embodiment, in which a clamp section is closed to the distal portion of a vibration transmission member to complete cutting a living tissue.

As shown in FIG. 8A, the main body 52 includes an extension 372 that extends in a direction opposite to the treatment surface 26b and the clamp section 28 with the rotation shaft 62 between the extension 372 and the clamp section 28. The pressing member 72 is placed on the extension 372. The extension 372 has a surface opposed to the vibration transmission member 26. The pressing member 72 is placed on this opposed surface.

When the clamp section 28 rotates on the rotation shaft 62 and comes close to the vibration transmission member 26 and the treatment surface 26b is brought into contact with the vibration transmission member 26, the extension 372 also comes close to the vibration transmission member 26 and the pressing member 72 is brought into contact with the vibration transmission member 26. In this case, the direction of pressing force applied to the vibration transmission member 26 by the pressing member 72 and the direction of pressing force applied to the vibration transmission member 26 by the treatment surface 26b are opposite to each other. The vibration transmission member 26 is not easily bent because the vibration transmission member 26 is hard against the clamp section 28. Thus, when the vibration transmission member 26 is pressed by the pressing member 72, reaction force loaded to the extension 372 from the vibration transmission member 26 through the pressing member 72 inhibits the vibration transmission member 26 from being pressed by the pressing member 72. Therefore, part of the pressing force applied to the vibration transmission member 26 by the pressure pad 54 of the clamp section 28, which moves in association with the extension 372, is canceled to weaken the pressing force applied to the treatment surface 26b of the vibration transmission member 26 by the pressure pad 54. Consequently, the pressure pad 54 can be prevented from being worn due to the vibration of the vibration transmission member 26.

Figure 8B:
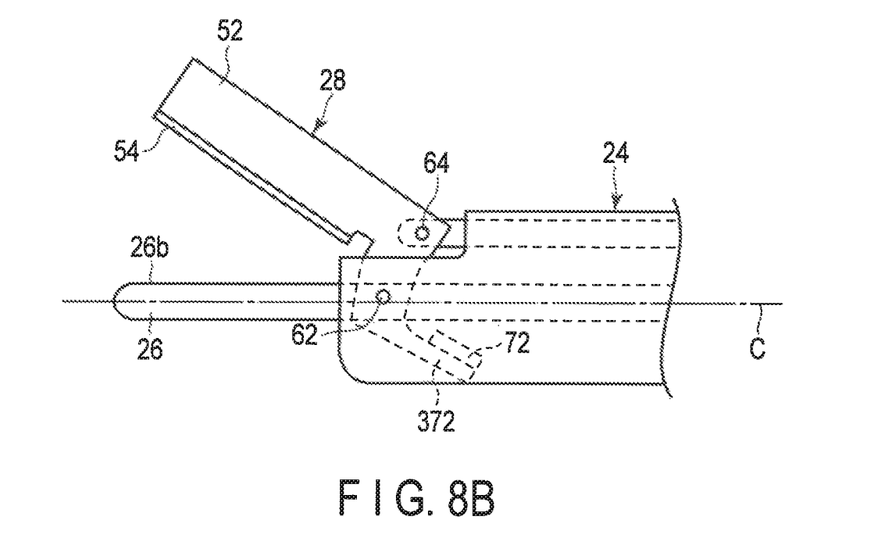
FIG. 8B is a schematic view of the surgical instrument according to the fourth embodiment, in which the clamp section is opened to the distal portion of the vibration transmission member.

When the clamp section 28 is disposed in a position distal from the vibration transmission member 26 as shown in FIG. 8B, the extension 372 is separated from the vibration transmission member 26. The pressing member 72 is also separated from the vibration transmission member 26.

Figure 8C:
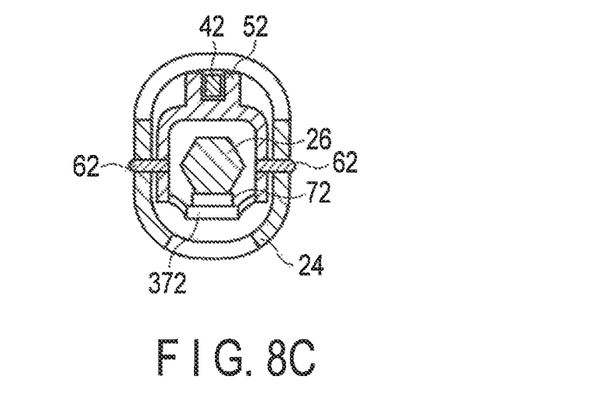
FIG. 8C is a schematic cross-sectional view taken along line 8C-8C of FIG. 8A.

As shown in FIG. 8C, the distal portion 24a of the sheath is notched so as not to interfere with the extension 372, thereby allowing the extension 372 to rotate in accordance with the rotation of the clamp section 28.

Even with the use of the structure in which the clamp section 28 is opened to the vibration transmission member 26 when the driving member 42 advances, and the clamp section 28 is closed to the vibration transmission member 26 when the driving member 42 is retreated as described in the modification to the first embodiment, the relationship between the pin 174 and the guide 172 can be adopted as well, as can be the relationship between the cam pin 272 and the cam groove 282.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical instrument comprising:
a clamp section main body which is movable between a close position that is close to a vibration transmission member and an away position that is away from the vibration transmission member;
a pressure pad provided on the clamp section main body and provided on a position that is close to the vibration transmission member, the pressure pad being brought into contact with the vibration transmission member when the clamp section main body is in the close position; and
a pressing member which is configured to press the vibration transmission member in association with the clamp section main body coming close to the close position, and is configured to decrease pressure of contact between the pressure pad and the vibration transmission member,
wherein:
the pressing member is movable between a pressing position in which the vibration transmission member is pressed, and a pressing release position in which pressing on the vibration transmission member is released, in association with movement of the clamp section main body, and
the pressing member is configured to move toward the pressing release position from the pressing position in association with movement of the clamp section main body toward the away position from the close position.

2. The surgical instrument according to claim 1, wherein the pressure pad is continuously in contact with the vibration transmission member in the close position.

3. The surgical instrument according to claim 1, wherein the pressing member includes a contact surface that is configured to contact the vibration transmission member and that is harder than the pressure pad.

4. The surgical instrument according to claim 1, comprising a driving member which is configured to move the clamp section main body between the close position and the away position,
wherein the driving member includes a pressing portion which is configured to press the pressing member on the vibration transmission member in association with the clamp section main body moving to the close position.

5. The surgical instrument according to claim 4, wherein the pressing member includes a contact surface that is configured to contact the vibration transmission member and a pressing surface that is configured to be pressed on the pressing portion of the driving member.

6. The surgical instrument according to claim 4, wherein:
the pressing portion of the driving member includes a cam groove; and
the pressing member includes a cam pin which is provided in the cam groove, which is configured to press the pressing member on the vibration transmission member in association with the driving member moving the clamp section main body to the close position and configured to release pressing on the vibration transmission member by the pressing member in association with the clamp section main body moving to the away position.

7. The surgical instrument according to claim 1, wherein the pressing member includes a guide which is configured to move the pressing member with respect to the vibration transmission member within a predetermined range.

8. The surgical instrument according to claim 7, comprising a sheath provided with the pressing member at a proximal side of the sheath with respect to a distal end of the sheath,
wherein a moving range of the pressing member with respect to the sheath is defined by the guide.

9. The surgical instrument according to claim 1, comprising:
a driving member which is configured to move the clamp section main body between the close position and the away position; and
a sheath which covers a periphery of the driving member and is provided with the pressing member at a proximal side of the sheath with respect to a distal end of the sheath.

10. The surgical instrument according to claim 1, wherein:
the vibration transmission member has a length such that a distal end of the vibration transmission member is set in a vibration antinode position when an ultrasonic vibration is transmitted to the vibration transmission member by causing an ultrasonic transducer, which is disposed at a proximal end of the vibration transmission member, to generate a vibration; and
the pressing member is disposed on a vibration node position when the ultrasonic vibration is transmitted to the vibration transmission member.

11. A surgical instrument unit comprising:
the surgical instrument according to claim 1; and
an ultrasonic transducer which is provided at a proximal end of the vibration transmission member and which is configured to transmit an ultrasonic vibration to the vibration transmission member.

* * * * *